United States Patent [19]

Cure

[11] 4,120,204
[45] Oct. 17, 1978

[54] DEVICE FOR COLLECTING SAMPLES OF MOLTEN METALS

[75] Inventor: Omer P. Cure, Diepenbeek, Belgium

[73] Assignee: Electro-Nite Co., Philadelphia, Pa.

[21] Appl. No.: 819,308

[22] Filed: Jul. 27, 1977

Related U.S. Application Data

[63] Continuation-in-part of Ser. No. 723,360, Sep. 15, 1976, Pat. No. 4,037,478.

[51] Int. Cl.² .............................................. G01N 1/12
[52] U.S. Cl. .................................................. 73/425.4 R
[58] Field of Search ........................ 73/425.4, DIG. 9

[56] References Cited

U.S. PATENT DOCUMENTS 3,913,404  10/1975  Boron ........................... 73/425.4 R
3,915,014  10/1975  Judge ............................ 73/425.4 R Primary Examiner—S. Clement Swisher
Attorney, Agent, or Firm—Seidel, Gonda & Goldhammer

[57] ABSTRACT

The entrance on a sampling device for molten metal is defined in part by a tube made from a deoxidizing agent such as aluminum. The tube melts as a sample of molten bath passes therethrough to a collecting chamber so that all portions of the sample are deoxidized uniformly.

9 Claims, 8 Drawing Figures

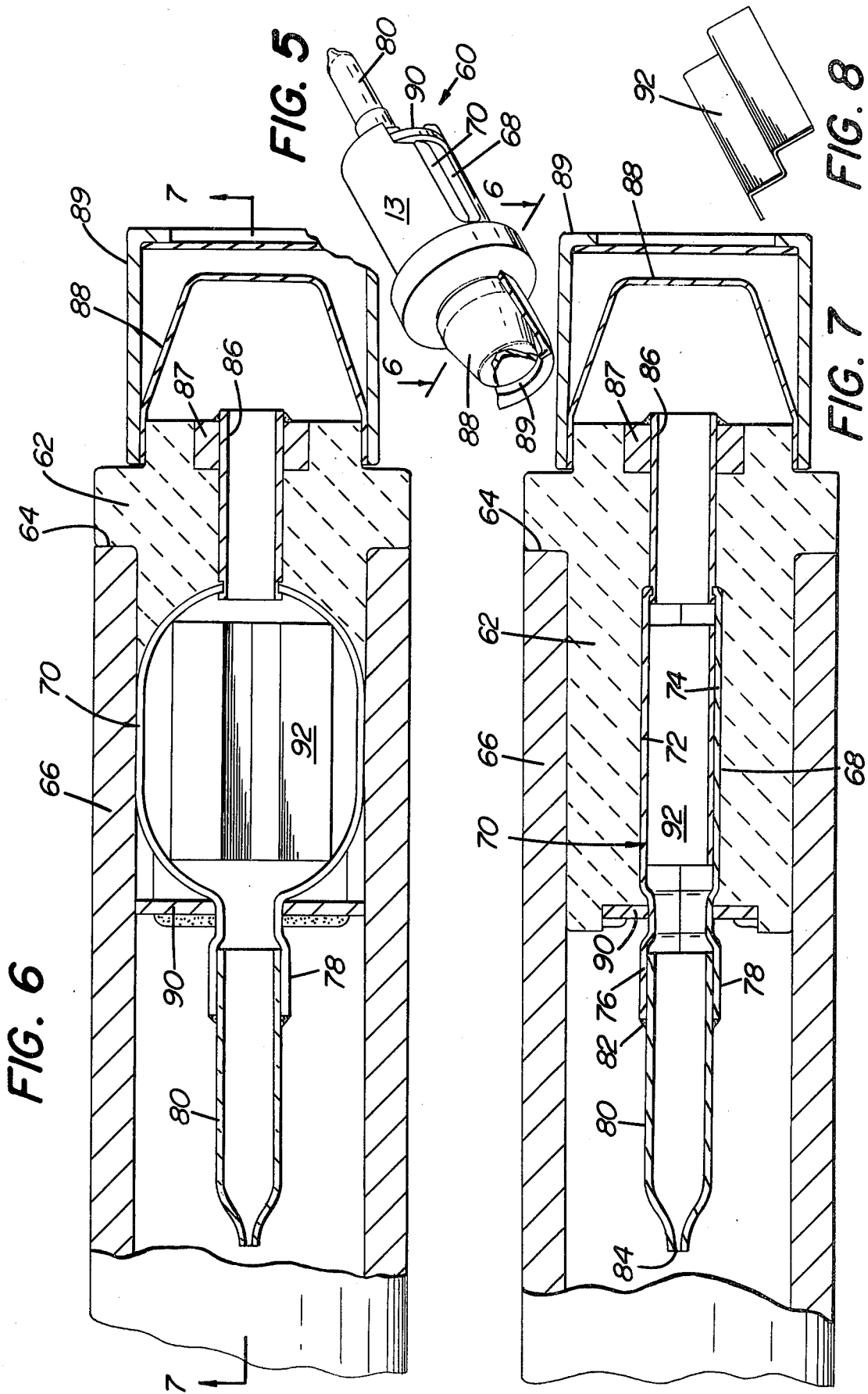

DEVICE FOR COLLECTING SAMPLES OF MOLTEN METALS

RELATED CASE

This application is a continuation-in-part of application Ser. No. 723,360 filed Sept. 15, 1976 on "Device For Collecting Samples of Molten Metals" now U.S. Pat. No. 4,037,478.

BACKGROUND

U.S. Pat. Nos. 3,369,406; 3,646,816 and 3,805,621 are considered representative of the prior art. Numerous devices for collecting samples from a bath of molted metal have been proposed heretofore. One of the problems involved in such devices is the uneven distribution of a deoxidizing agent in the sample.

It is common to provide a deoxidizing agent, such as aluminum in the shape of wire or a tube, along the entrance of or in a sampling device for contact with the molten metal sample. When the molten metal enters the sampling device, the deoxiding agent is almost immediately melted away so as to result in the initial portion of the sample being deoxidized whereas the last portion of the sample to enter the chamber has virtually no deoxidation.

Another problem involved in using prior art devices relates to a loss of the sample when the sampling device is withdrawn from the bath. In this regard, the entrance to the sampling chamber is below the sampling chamber and the sampling device is upright when introduced into the molten bath. Thus, it has been noted that withdrawal of the sampling device from the bath results in a portion of the sample returning to the bath. Another problem with the prior art relates to disassembly of the components to attain access to the specimen. The above and other disadvantages of the prior art are solved by the present invention.

SUMMARY OF THE INVENTION

The device for collecting a sample of molten metal in accordance with the present invention includes a body having a chamber therein. A vessel is provided in said chamber. A filling conduit is supported by the body and has one end communicating with said vessel. Deoxidizing material is provided adjacent one end of said conduit. A metal cooling ring is provided to inhibit loss of a sample as the device is withdrawn from the molten metal.

In a preferred embodiment of the present invention, the body of the device is split longitudinally and temporarily bonded together during assembly with a material such as a hot metal adhesive which will be rendered ineffective by the temperature of a bath. When a body is removed from its manipulating support such as a cardboard tube, the body on impact will separate into the two discrete halves. At the same time, the sampling retrieval vessel will separate into two halves, and the speciman will separate from the other components. In this manner, retrieval of the sample is attained merely by causing the body to fall a distance of several feet onto a concrete floor.

It is another object of the present invention to provide a device for collecting a sample of molten metal which enables the sample to be easily retrieved without disassembly of any components.

Other objects will appear hereinafter.

For the purpose of illustrating the invention, there is shown in the drawings a form which is presently preferred; it being understood, however, that this invention is not limited to the precise arrangements and instrumentalities shown.

FIG. 5 is a perspective view of another embodiment of the present invention.

FIG. 6 is a sectional view taken along the line 6—6 in FIG. 5.

FIG. 7 is a sectional view taken along the line 7—7 in FIG. 6.

FIG. 8 is a perspective view of deoxidizing material.

Referring to the drawing in detail, wherein like numerals indicate like elements, there is a device in accordance with the present invention designated generally as 10.

Figure 1:
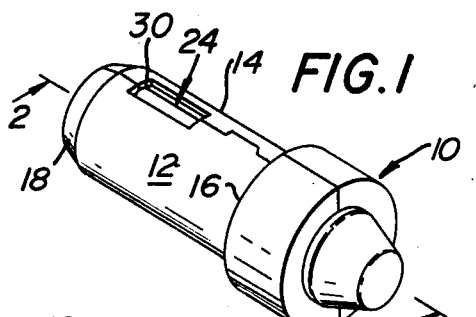
FIG. 1 is a perspective view of a device for collecting samples of molten metal in accordance with the present invention.
Figure 2:
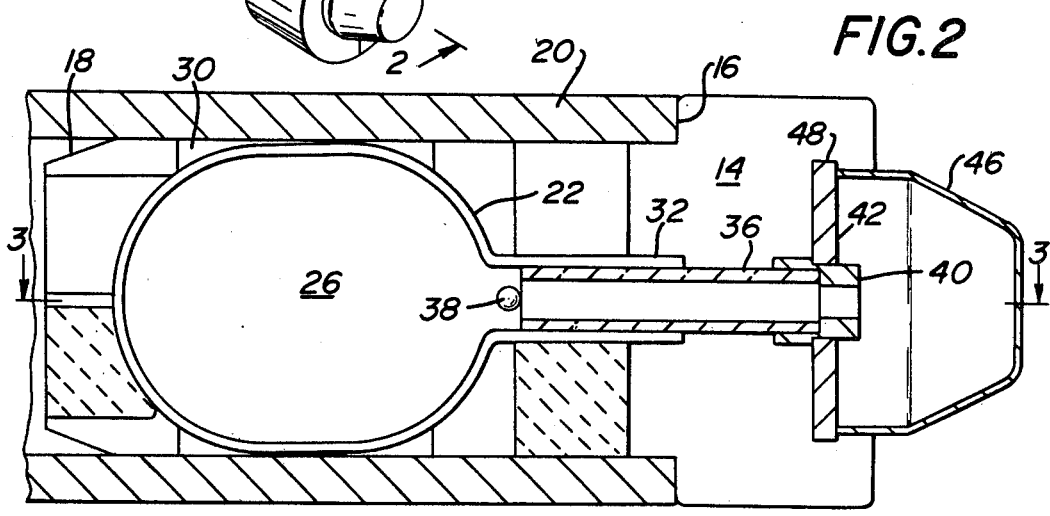
FIG. 2 is a sectional view taken along line 2—2 in FIG. 1, with the device mounted in one end of a support such as a cardboard tube.
Figure 3:
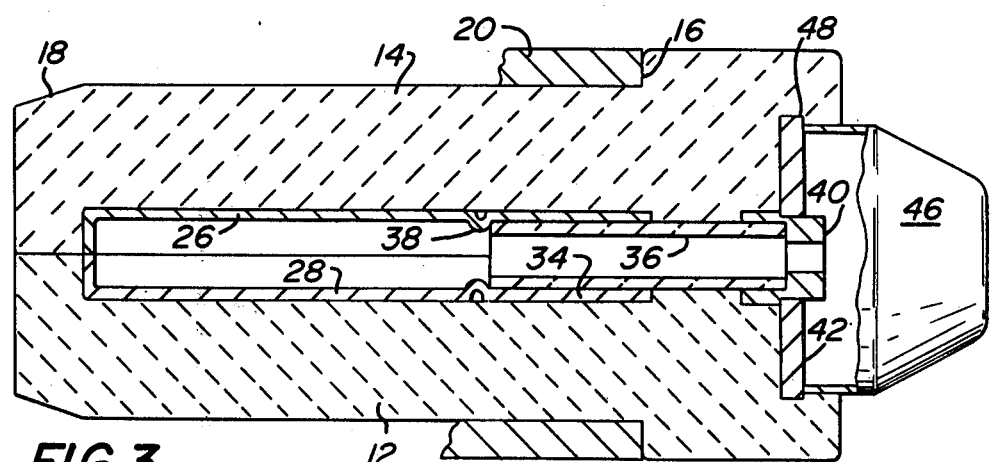
FIG. 3 is a sectional view taken along the line 3—3 in FIG. 2.

The device 10 includes a body made from a refractory material which is inexpensive and fractures easily such as foundry sand. The body of the device 10 is preferably made with mating halves 12 and 14. An enlarged head on one end of the body defines a shoulder 16 for contact with one end of a support such as cardboard tube 20. The other end of the body is provided with a taper 18 to facilitate the ease of introduction of the device 10 into the cardboard tube 20.

The two halves, prior to introduction into the tube 20, are retained in assembled relationship by use of spots of adhesive such as a hot melt adhesive on the juxtaposed faces of the body halves 12 and 14. Such adhesive facilitates the ease of handling and assembling of the device 10 into the cardboard tube 20. The outer diameter of the device 10 is such that it is a slight force-fit with respect to the inner diameter of tube 20. In this manner, the tube 20 may be held in an upright position and the device 10 will not fall out or separate even though the adhesive is no longer effective. It will be noted that the head on the immersion end of the device 10 is of substantially the same diameter as the outer diameter of tube 20.

The body of the device 10 is provided internally with a chamber 22 within which is disposed a vessel 24. As shown more clearly in FIG. 1, the device 10 is provided with an opening 30 at the parting line of the body halves whereby the vessel 24 is visible. The vessel 24 is preferably a metal vessel made from separable halves 26 and 28. The halves 26 and 28 have mating semi-circular stems 32, 34, respectively.

A conduit 36 having a smooth inner peripheral surface and made from a frangible refractory material such as quartz is provided. One end of the conduit 36 communicates with the interior of the vessel 24 and abuts against the limit stop dimples 38. A tube 40 of a deoxidizing material such as aluminum may be coaxial with the other end of conduit 36. The inner diameter of tube 40 is less than the inner diameter of conduit 36 but has a thicker wall than conduit 36. Tube 40 has an extension surrounding the conduit 36.

A metal ring 42 is coupled to the tube 40. Preferably, ring 42 is force-fit onto the outer periphery of tube 40 and abuts against a shoulder on the tube extension. Ring 42 is made from a material such as iron or steel and has a melting temperature substantially higher than the melting temperature of aluminum. A cap 46 has its open end in contact with the ring 42 and is disposed along the longitudinal axis of the device 10. The body halves 12 and 14 are notched for receiving the periphery of ring 42 to thereby position tube 40 in a predetermined position against one end of the conduit 36. Cap 46 is made from a low temperature melting material or is thin walled and merely provides protection when the device 10 is introduced through a slag layer.

The manner in which the devices of the general type involved herein are utilized is well known to those skilled in the art. Hence, only a brief discussion is deemed necessary. The tube 20 is grasped by an operator and the immersion end thereof containing the device 10 is introduced through the slag into a bath of molten metal. The cap 46 is melted during passage through the slag. Molten metal flows through tube 40, through conduit 36, into the vessel 24. Any air in the vessel 24 is expelled through the gap between the mating halves and through the opening 30 into the interior of the cardboard tube 20.

As the molten metal flows through the tube 40, the tube 40 is melted along its inner peripheral surface thereby deoxidizing the molten metal. The tube 40 has sufficient mass whereby it does not melt away until the vessel 24 and 36 have been filled with molten metal. Hence, even the last portion of the molten metal forming a part of the sample to be retrieved will be deoxidized.

The ring 42 acts as a cooling body for the portion of the tube 40 which remains after a complete sample has been obtained. It has been discovered that the ring 42 has a cooling effect on the tube 40 whereby none of the sample flows out of the conduit 46 upon withdrawal of the device 10 from the bath.

Since the adhesive retaining the body halves 12 and 14 together is no longer effective, the force fit of the device 10 within the cardboard tube 20 is the only force retaining the device 10 in an assembled relationship. Application of force for ejecting the device 10 from the immersion end of the tube 20 may be accomplished in any one of a wide variety of manners. Upon such ejection, the device 10 is permitted to fall at least several feet onto a concrete floor. Upon impact with the floor, the body of the device 10 separates along the parting line, the vessel 24 separates into two halves and the conduit 36 breaks or is easily broken to thereby expose the specimen which has the general shape of a lollipop with flat sides, a stem and a generally oval configuration.

Figure 4:
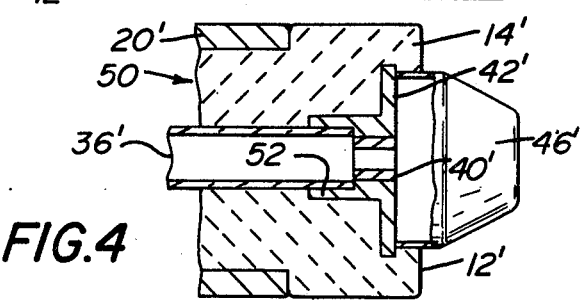
FIG. 4 is a view similar to FIG. 3 but on a smaller scale and showing an alternative embodiment of the present invention.

In FIG. 4, there is illustrated another embodiment of the present invention which is identical with that described above except as will be made clear hereinafter. Hence, corresponding elements are provided with corresponding primed numerals. The device designated as 50 differs from the embodiment set forth above in that the ring 42' has an extension or boss 52 which is telescoped over the inlet end of the conduit 36'. The tube 40' of deoxidizing material is force-fit into the ID of the ring 42'.

Referring to FIGS. 5-8 of the drawing, there is shown another device in accordance with the present invention designated generally as 60. Device 60 is the same as device 10 except as may be set forth hereinafter.

The device 60 includes a body 62 made from a refractory material which is inexpensive and fractures easily such as foundry sand. The body 62 of the device 60 is preferably cast in one piece. An enlarged head on one end of the body defines a shoulder 64 for contact with one end of a support such as paperboard tube 66. The other end of the body is provided with a taper to facilitate the ease of introduction of the device 60 into tube 66.

The outer diameter of the device 60 is such that it has a slight force fit with respect to the inner diameter of tube 66. In this manner, the tube 66 may be held in an upright position and the device 60 will not fall out. It will be noted that the head on the immersion end of the device 60 is of substantially the same diameter as the outer diameter of tube 66.

The body 62 of the device 60 is provided internally with a chamber defined by slot 68 exposed on opposite sides of body 62 and within which is disposed a vessel 70. The vessel 70 is preferably a metal vessel made from separable halves 72 and 74. The halves 72 and 74 have mating semi-circular stems 76, 78, respectively.

A conduit 80 having a smooth inner peripheral surface and made from a frangible refractory material such as quartz is provided. One end of the conduit 80 communicates with the interior of the vessel 70 and is supported by stems 76, 78 against the limit stop dimples. Adhesive or cement 82 joins conduit 80 to stems 76, 78. The other end of conduit 80 is tapered to a small air vent hole 84. The hole 84 allows air to escape into tube 66 as metal enters conduit 80.

A filling conduit 86 is removably coupled to the vessel 70. Preferably, conduit 86 has a peripheral notch which receives the walls of mating halves 72, 74. A refractory cement seal 87 is applied between body 62 and the end portion of conduit 86. Conduit 86 has a minimum length of 5 mm, a maximum internal diameter of 9 mm, and a minimum wall thickness of 0.5 mm so as to have sufficient mass to act as a cooling means for inhibiting flow out of conduit 86 upon withdrawal of device 10 from the bath. Conduit 86 is made from a material such as iron or steel, is shorter than conduit 80, and is diametrically opposite conduit 80. One end of conduit 86 is flush with or projects slightly beyond an end face on body 62.

A metal cap 88 has its open end in contact with an axial projection on body 62 so as to be disposed along the longitudinal axis of conduit 86 and the device 60. Cap 88 is made from a low temperature melting material or is thin walled and merely provides protection when the device 60 is introduced through a slag layer. A paper cap 89 surrounds cap 88 and prevents slag from attaching to cap 88.

Vessel 70 is retained in slot 68 by a retainer 90 bonded to the end portion of the two body projections. Retainer 90 has a hole or slot through which the stems 76, 78 extend. If desired, retainer 90 may be eliminated and refractory cement applied to hold vessel 70 in slot 68. Deoxidizing material 92, preferably of a corrugated shape, is placed in the chamber of vessel 70 with the corrugations generally parallel to the axis of conduit 88. Material 92 deoxidizes the specimen from vessel 70 and conduit 80 and may be aluminum, titanium, zirconium, etc.

Device 60 is used in the same manner as device 10 but produces a lollipop specimen having projections extending in opposite directions. The specimen projection from conduit 80 will have a smooth outer surface and will be used as a specimen for lab analysis. The specimen projection from conduit 86 has less uniformity due to slight loss of metal when the device is withdrawn from the bath and therefore is generally not used for lab analysis. The presence of the specimen projection from conduit 86 assures that the projection from conduit 80 will be suitable for reliable lab analysis. Since conduit 80 is not surrounded by body 62, the specimen therein cools more quickly than the specimen in vessel 70.

Thus, it will be seen that the devices of the present invention are structurally interrelated in a manner so as to readily separate into components to facilitate access to the specimen while at the same time will provide a specimen which is uniformly homogeneous.

The present invention may be embodied in other specific forms without departing from the spirit or essential attributes thereof and, accordingly, reference should be made to the appended claims, rather than to the foregoing specification as indicating the scope of the invention.

It is claimed:

1. A device for collecting a sample of molten metal comprising a non-metallic refractory body having a chamber therein, a vessel in said chamber and comprised of mating portions which are readily separable, a filling conduit supported by said body and having one end communicating with one end of said vessel, the other end of said conduit terminating adjacent an end face at the immersion end of said body, a second conduit made from a frangible material, one end of said second conduit communicating with said vessel at the opposite end of the vessel from said first conduit, and at least a major portion of said second conduit projecting beyond the end face of said body at the end of said body opposite said immersion end of the body, and transverse dimensions of said chamber being at least as large as the transverse dimensions of said conduits, and deoxidizing material supported by at least one of said vessel and conduits, said filling conduit being of metal and releasably connected to each of the mating portions of said vessel.

2. A device in accordance with claim 1 including a metal cap supported by said body for protecting said one end of said filling conduit when the device is immersed into a bath of molten metal, and a paper cup around said metal cap.

3. A device for collecting a sample of molten metal comprising an expendable tubular support having an immersion end, a sampling device mounted in said immersion end, said device including a fracturable, non-metallic body having a chamber therein with slots on opposite sides of the body, a vessel separable into components, said vessel being disposed within said chamber and exposed at said slots, the vessel being generally oval shaped, said body having a shoulder, an end face of said tubular support engaging said shoulder, a filling conduit supported by said body, said filling conduit having one end communicating with said vessel, the other end of said filling conduit terminating adjacent an end face of said body, a protective metal cap supported by said body for protecting said other end of said filling conduit when the immersion end of said body is introduced through a layer of slag, and cooling means for inhibiting flow of metal from said filling conduit when the sampling apparatus is withdrawn from a bath of molten metal.

4. Sampling apparatus in accordance with claim 3 including a second conduit communicating at one end with said vessel, said second conduit and said first-mentioned conduit being generally coaxial, said second conduit projecting beyond an end face of said body so as to be surrounded by the air space within said tubular support, said second conduit being made from a frangible material.

5. Sampling apparatus in accordance with claim 3 including a paper cap around said metal cap.

6. Sampling apparatus in accordance with claim 5 wherein a major portion of said paper cap is spaced from said metal with an air space therebetween.

7. Sampling apparatus in accordance with claim 3 wherein said body is foundry sand.

8. A device for collecting a sample of molten metal comprising a tube having one end which is to be immersed in a bath of molten metal, a vessel supported in said tube and comprised of mating portions which are readily separable, a filling conduit supported by said tube, said conduit having one end communicating with and releasably connected to each of the mating portions of said vessel, the other end of said conduit terminating adjacent an end face at the immersion end of said tube, said filling conduit being of metal and having sufficient mass so as to act as a cooling means for inhibiting flow upon withdrawal of the device from a bath of molten metal.

9. A device for collecting a sample of molten metal comprising a hollow body having a chamber therein, a vessel in said chamber and comprised of mating portions which are readily separable, a filling conduit supported by said body and having one end communicating with one end of said vessel, said filling conduit being of metal and releasably connected at said one end to each of the mating portions of said vessel, the other end of said conduit terminating adjacent an end face at the immersion end of said body, a second conduit made from a frangible material, one end of said second conduit communicating with said vessel at the opposite end of the vessel from said first conduit, and at least a major portion of said second conduit projecting beyond the end face of said body at the end of said body opposite said immersion end of the body, transverse dimensions of said chamber being at least as large as the transverse dimensions of said conduits, and deoxidizing material supported by at least one of said vessel and conduits.

* * * * *